United States Patent [19]
Hermansky

[11] Patent Number: 5,538,936
[45] Date of Patent: Jul. 23, 1996

[54] REVERSIBLE AGRICULTURAL GEL AND PASTE FORMULATIONS

[75] Inventor: Clarence G. Hermansky, Wilmington, Del.

[73] Assignee: E. I. Du Pont de Nemours and Company, Wilmington, Del.

[21] Appl. No.: 325,263

[22] PCT Filed: Apr. 27, 1993

[86] PCT No.: PCT/US93/03711

§ 371 Date: Dec. 2, 1994

§ 102(e) Date: Dec. 2, 1994

[87] PCT Pub. No.: WO93/21763

PCT Pub. Date: Nov. 11, 1993

[51] Int. Cl.$^6$ .......... A01N 25/04; A01N 47/18; A01N 47/36; A01N 57/04

[52] U.S. Cl. .......... 504/116; 504/136; 504/206; 504/212; 504/213; 514/395; 514/494; 514/944; 71/DIG. 1

[58] Field of Search .......... 504/213, 133, 504/116, 136, 206, 212; 71/DIG. 1; 514/395, 494, 944

[56] References Cited

U.S. PATENT DOCUMENTS

| | | | |
|---|---|---|---|
| 3,157,486 | 11/1964 | Harrison et al. | 71/24 |
| 3,333,942 | 8/1967 | Hartley et al. | 71/93 |
| 3,671,215 | 6/1972 | Bellsmith et al. | 71/97 |
| 3,930,838 | 1/1976 | Pellegrini et al. | 71/100 |
| 4,501,605 | 2/1985 | Hough et al. | 504/217 |
| 4,707,189 | 11/1987 | Nickol | 106/176 |
| 4,800,036 | 1/1989 | Rose et al. | 252/102 |
| 4,808,215 | 2/1989 | Gill et al. | 71/105 |
| 4,910,248 | 3/1990 | Peiffer | 524/535 |
| 4,936,900 | 6/1990 | Hyson | 71/90 |
| 5,078,732 | 1/1992 | Neilsen et al. | 504/217 |
| 5,139,152 | 8/1992 | Hodakowski et al. | 71/DIG. 1 |
| 5,149,358 | 9/1992 | Bernard | 504/135 |

FOREIGN PATENT DOCUMENTS

| | | |
|---|---|---|
| 0124295 | 11/1984 | European Pat. Off. . |
| 0237418 | 9/1987 | European Pat. Off. . |
| 0388239 | 9/1990 | European Pat. Off. . |
| 2146504 | 3/1973 | France . |

OTHER PUBLICATIONS

Miyamoto, J. et al., "Pesticide Chemistry: Human Welfare and the Environment", *International Union of Pure Applied Chemistry*, 4, 245–256, Aug. 29—Sep. 4, 1982.

Shaw, Duncan J., *Introduction to Colloid and Surface Chemistry*, 206 (1966).

*Primary Examiner*—S. Mark Clardy

[57] ABSTRACT

A thixotropic pesticide formulation which is water-based and relies on electroytic differences among formulation ingredients to maintain thixotropy, and to a method for using the formulations to control crop pests.

10 Claims, No Drawings

REVERSIBLE AGRICULTURAL GEL AND PASTE FORMULATIONS

BACKGROUND OF THE INVENTION

This application is a national stage application filed under 35 USC 371, on Dec. 2, 1994, from PCT/US93/03711, filed Apr. 27, 1993.

Aqueous suspensions of pesticides are well known in the art. For example, see International Union of Pure and Applied Chemistry (Applied Chemistry Division) "Pesticide Chemistry: Human Welfare and the Environment" Proceedings of the 5th International Congress of Pesticide Chemistry, Kyoto, Japan, 29 Aug.–4 Sep. 1982. The use of inorganic salts to reduce the solubility of an otherwise soluble pesticide acid, base or salt causing precipitation of the pesticide acid, base or salt, a process known as "salting-out," is also known in the art and traditionally taught in university Chemistry and Engineering Thermodynamics courses. For example, see D. J. Shaw, "Introduction to Colloid and Surface Chemistry," London Butterworths, 1966.

U.S. Pat. No. 4,936,900 teaches the use of carboxylic or inorganic acid salts to chemically stabilize sulfonylurea pesticides, or agriculturally suitable sulfonylurea salt dispersions.

Not disclosed or suggested in the prior art and the subject of the present invention are compositions of pesticides which are aqueous based, physically reversible structured-fluids which flow on application of shear and which spontaneously rebuild structure on standing.

SUMMARY OF THE INVENTION

This invention concerns a thixotropic pesticidal formulation comprising a pesticidal component, a structuring agent, and the balance to 100% being an aqueous medium wherein:

the pesticidal component is selected from the group:
a) a soluble electrolyte,
b) a soluble non-electrolyte,
c) an insoluble electrolyte, and
d) an insoluble non-electrolyte; and the structuring agent is at least one anionic or cationic member selected from the group:
e) a polyelectrolyte,
f) a surfactant, and
g) a suspending agent; provided that:
  (i) when the pesticidal component is a), b) or d), then the structuring agent is g) and at least one of e) and f), such that e) and g) bear dissimilar charges, or when e) is not present, f) and g) bear dissimilar charges;
  (ii) when the pesticidal component is c), then the structuring agent is selected from at least one of e) and f), such that e) and c) bear dissimilar charges, or when e) is not present, f) and c) bear dissimilar charges;

the ingredients being present in the following amounts based on total weight of the formulation:
1–60% pesticidal component;
0.1–20% of at least one of a polyelectrolyte and a surfactant;
0–20% suspending agent; the combination of pesticidal component, polyelectrolyte, surfactant, and suspending agent comprising at least 4%; and
35–96% aqueous medium.

The term "pesticidal component" is meant to include any chemical used for crop protection or mixture of said chemicals. More specifically, ingredients are selected from the class of herbicides, fungicides, bactericides, insecticides, insect antifeedants, acaricides, miticides, nematocides and plant growth regulants. Herbicides include sulfonylurea herbicides which are meant to include the entire class of herbicides containing the following and any closely related chemical functionalities:

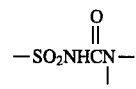

Pesticidal components which are classified as "electrolytes" dissociate (separate) into two or more ions in water. Conversely, "non-electrolytes" do not dissociate in water.

Suitable "polyelectrolytes" of the invention can be either cationic or anionic, and include all water-swellable or water-soluble polymers which bear more than one ionic functional group per each macromolecule.

"Surfactants" consist of molecules lower in molecular weight than polyelectrolytes which are surface active and which bear one or two charges per molecule.

A "suspending agent" can be clay and oxide particulates which are traditionally used to retard settling in both aqueous and non-aqueous based suspensions.

"Dissimilar charge" is defined such that the electronic energy of the substances are of different signs. Electrolytes, polyelectrolytes, surfactants, and suspending agents which have cationic polymer or surface-active portions are positively charged [i.e., sign is (+)], those which have anionic polymer or surface-active portions are negatively charged [i.e., sign is (–)], and pesticides which are non-electrolytes are not charged (i.e., neutral). For example, a cationic polyelectrolyte has a dissimilar charge to an anionic suspending agent and to a non-electrolyte pesticide. Conversely, two cationics or two non-electrolytes would have similar charge.

This invention also concerns a method for protecting crops comprising applying to the crops, to the environment of the crops, or to the pests, an effective amount of the formulation of this invention to control the particular pest of interest.

Preferred compositions (Preferred 1) of those described above are thixotropic pesticidal formulations wherein the ingredients are present in the following amounts based on total weight of the formulation:
10–50% pesticidal component;
0.1–10% at least one of a polyelectrolyte and a surfactant;
0–15% suspending agent; and
35–96% aqueous medium.

More preferred compositions (Preferred 2) are compositions of Preferred 1 wherein the pesticidal component is a sulfonylurea herbicide and the ingredients are present in the following amounts based on total weight of the formulation:
10–40% sulfonylurea;
0.1–5% at least one of a polyelectrolyte and a surfactant;
0–10% suspending agent;
5–25% agriculturally suitable stabilizing salt, such that the sulfonylurea and stabilizing salt are less than 85% by total formulation weight; and
35–96% aqueous medium.

Even more preferred compositions (Preferred 3) are compositions of Preferred 1 wherein the pesticidal component comprises a sulfonylurea herbicide and a non-sulfonylurea pesticide in the following amounts based on total weight of the formulation:

10–40% sulfonylurea and non-sulfonylurea pesticide;
0.1–5% at least one of a polyelectrolyte and a surfactant;
0–10% suspending agent;
5–25% agriculturally suitable stabilizing salt, such that the sulfonylurea, non-sulfonylurea pesticide and stabilizing salt are less than 85% by total formulation weight; and
35–96% aqueous medium.

The "agriculturally suitable stabilizing salts" include organic or inorganic salts which can be used to salt-out otherwise water-soluble ionic pesticides thereby rendering them insoluble. In the case of sulfonylurea herbicides, wherein chemical stabilization can be achieved by the addition of salts, agriculturally suitable salts refer to carboxylic or inorganic acid salts with a solubility in water of greater than or equal to 3% at 5° C. and pH 6–10, and further provided that a 0.1 molar solution of the carboxylic or inorganic acid salt is between pH 6 and 10.

Even more preferred compositions (Preferred 4) are compositions of Preferred 2 wherein the polyelectrolytes or charged surfactants are selected from the group consisting of: quaternary polyelectrolytes or surfactants, and quaternary ammonium salts which may be protonated, ethoxylated or alkylated; polyacrylamides, such as aminomethylated polyacrylamide polymer having pendant dialkylated ammonium salt groups; primary, secondary or tertiary polyamines, such as ethoxylated octadecylamine-octadecylguanidine complexes; and primary secondary or tertiary amine surfactants with or without ethoxylation, protons or alkyl groups.

More preferred compositions (Preferred 5) are those of Preferred 4 wherein the polyelectrolytes are selected from the group consisting of: polymers having pendant acid functionality and the ability to form salts; anionic polyacrylamides and acrylamide copolymers, such as the sodium salt of 2-propenamide, 2-propenoic acid; polycarbonates, such as polyacrylic acid, polymethacrylic and styrene maleic anhydride acid polymers and copolymers; polysulfonates, such as lignosulfonates and sulfonated polystyrene; and polyphosphates.

Also preferred (Preferred 6) are compositions of Preferred 1 wherein the pesticidal component is a herbicide.

Also preferred (Preferred 7) are compositions of Preferred 3 wherein the mixture comprises a sulfonylurea herbicide and 3,5-dibromo-4-hydroxybenzonitrile (bromoxynil).

Even more preferred (Preferred 8) are compositions of Preferred 5 wherein the sulfonylurea herbicide is a compound of Formula I

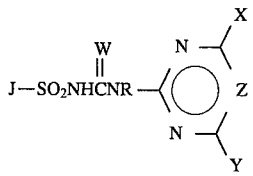

wherein:
J is

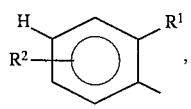  J-1

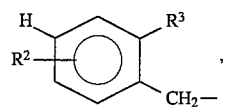  J-2

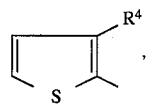  J-3

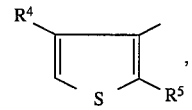  J-4

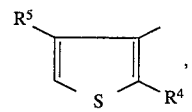  J-5

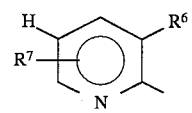  J-6

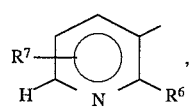  J-7

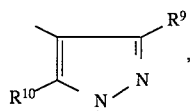  J-8

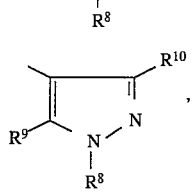  J-9

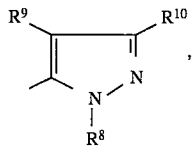  J-10

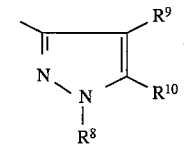  J-11

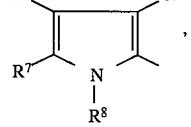  J-12

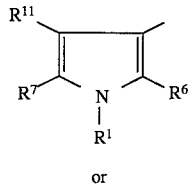  J-13 or

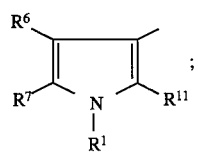

R is H or CH$_3$;

R$^1$ is F, Cl, Br, NO$_2$, C$_1$–C$_4$ alkyl, C$_1$–C$_4$ haloalkyl, C$_3$–C$_4$ cycloalkyl, C$_2$–C$_4$ haloalkenyl, C$_1$–C$_4$ alkoxy, C$_1$–C$_4$ haloalkoxy, C$_2$–C$_4$ alkoxyalkoxy, CO$_2$R$^{12}$, C(O)NR$^{13}$R$^{14}$, SO$_2$NR$^{15}$R$^{16}$, S(O)$_n$R$^{17}$, C(O)R$^{18}$, CH$_2$CN or L;

R$^2$ is H, F, Cl, Br, CN, CH$_3$, OCH$_3$, SCH$_3$, CF$_3$ or OCF$_2$H;

R$^3$ is Cl, NO$_2$, CO$_2$CH$_3$, CO$_2$CH$_2$CH$_3$, SO$_2$N(CH$_3$)$_2$, SO$_2$CH$_3$, SO$_2$CH$_2$CH$_3$, OCH$_3$, or OCH$_2$CH$_3$;

R$^4$ is C$_1$–C$_3$ alkyl, C$_1$–C$_2$ haloalkyl, C$_1$–C$_2$ alkoxy, C$_2$–C$_4$ haloalkenyl, F, Cl, Br, NO$_2$, CO$_2$R$^{12}$, C(O)NR$^{13}$R$^{14}$, SO$_2$NR$^{15}$R$^{16}$, S(O)$_n$R$^{17}$, C(O)R$^{18}$ or L;

R$^5$ is H, F, Cl, Br or CH$_3$;

R$^6$ is C$_1$–C$_3$ alkyl, C$_1$–C$_2$ alkoxy, C$_2$–C$_4$ haloalkenyl, F, Cl, Br, CO$_2$R$^{12}$, C(O)NR$^{13}$R$^{14}$, SO$_2$NR$^{15}$R$^{16}$, S(O)$_n$R$^{17}$, C(O)R$^{18}$ or L;

R$^7$ is H, F, Cl, CH$_3$ or CF$_3$;

R$^8$ is H, C$_1$–C$_3$ alkyl or pyridyl;

R$^9$ is C$_1$–C$_3$ alkyl, C$_1$–C$_2$ alkoxy, F, Cl, Br, NO$_2$, CO$_2$R$^{12}$, SO$_2$NR$^{15}$R$^{16}$, S(O)$_n$R$^{17}$, OCF$_2$H, C(O)R$^{18}$, C$_2$–C$_4$ haloalkenyl or L;

R$^{10}$ is H, Cl, F, Br, C$_1$–C$_3$ alkyl or C$_1$–C$_2$ alkoxy;

R$^{11}$ is H, C$_1$–C$_3$ alkyl, C$_1$–C$_2$ alkoxy, C$_2$–C$_4$ haloalkenyl, F, Cl, Br, CO$_2$R$_{12}$, C(O)NR$^{13}$R$^{14}$, SO$_2$NR$^{15}$R$^{16}$, S(O)$_n$R$^{17}$, C(O)R$^{18}$ or L;

R$^{12}$ is C$_1$–C$_3$ alkyl optionally substituted by halogen, C$_1$–C$_2$ alkoxy or CN, allyl or propargyl;

R$^{13}$ is H, C$_1$–C$_3$ alkyl or C$_1$–C$_2$ alkoxy;

R$^{14}$ is C$_1$–C$_2$ alkyl;

R$^{15}$ is H, C$_1$–C$_3$ alkyl, C$_1$–C$_2$ alkoxy, allyl or cyclopropyl;

R$^{16}$ is H or C$_1$–C$_3$ alkyl;

R$^{17}$ is C$_1$–C$_3$ alkyl, C$_1$–C$_3$ haloalkyl, allyl or propargyl;

R$^{18}$ is C$_1$–C$_4$ alkyl, C$_1$–C$_4$ haloalkyl or C$_3$–C$_5$ cycloalkyl optionally substituted by halogen;

n is 0, 1 or 2;

L is

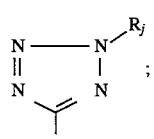

R$_j$ is H or C$_1$–C$_3$ alkyl;

W is O or S;

X is H, C$_1$–C$_4$ alkyl, C$_1$–C$_4$ alkoxy, C$_1$–C$_4$ haloalkoxy, C$_1$–C$_4$ haloalkyl, C$_1$–C$_4$ haloalkylthio, C$_1$–C$_4$ alkylthio, halogen, C$_2$–C$_5$ alkoxyalkyl, C$_2$–C$_5$ alkoxyalkoxy, amino, C$_1$–C$_3$ alkylamino or di(C$_1$–C$_3$ alkyl)amino;

Y is H, C$_1$–C$_4$ alkyl, C$_1$–C$_4$ alkoxy, C$_1$–C$_4$ haloalkoxy, C$_1$–C$_4$ alkylthio, C$_1$–C$_4$ haloalkylthio, C$_2$–C$_5$ alkoxyalkyl, C$_2$–C$_5$ alkoxyalkoxy, amino, C$_1$–C$_3$ alkylamino, di(C$_1$–C$_3$ alkyl)amino, C$_3$–C$_4$ alkenyloxy, C$_3$–C$_4$ alkynyloxy, C$_2$–C$_5$ alkylthioalkyl, C$_2$–C$_5$ alkylsulfinylalkyl, C$_2$–C$_5$ alkylsulfonylalkyl, C$_1$–C$_4$ haloalkyl, C$_2$–C$_4$ alkynyl, C$_3$–C$_5$ cycloalkyl, azido or cyano;

Z is CH or N;

and their agriculturally suitable salts; provided that:

(a) when X and/or Y is C$_1$ haloalkoxy, then Z is CH;

(b) when X is halogen, then Z is CH and Y is OCH$_3$, OCH$_2$CH$_3$, N(OCH$_3$)CH$_3$, NHCH$_3$, N(CH$_3$)$_2$ or OCF$_2$H.

Even more preferred (Preferred 9) are compositions of Preferred 8 wherein the herbicide is selected from the group:

2-chloro-N-[[(4-methoxy-6-methyl-1,3,5-triazin-2-yl)amino]carbonyl]benzenesulfonamide (chlorsulfuron);

methyl 2-[[[[(4,6-dimethyl-2-pyrimidinyl)amino]carbonyl]amino]sulfonyl]benzoate (sulfometuron methyl);

ethyl 2-[[[[(4-chloro-6-methoxy-2-pyrimidinyl)amino]carbonyl]amino]sulfonyl]benzoate (chlorimuron ethyl);

methyl 2-[[[[(4-methoxy-6-methyl-1,3,5-triazin-2-yl)amino]carbonyl]amino]sulfonyl]benzoate (metsulfuron methyl);

methyl 2-[[[[(4,6-dimethoxy-2-pyrimidinyl)amino]carbonyl]amino]sulfonyl]-6-(trifluoromethyl)-3-pyridinecarboxylate (ethametsulfuron methyl);

methyl 2-[[[[(4-ethoxy-6-(methylamino)-1,3,5-triazin-2-yl)amino]carbonyl]amino]sulfonyl]benzoate;

2-(2-chloroethoxy)-N-[[(4-methoxy-6-methyl-1,3,5-triazin-2-yl)amino]carbonyl]benzenesulfonamide;

ethyl 5-[[[[(4,6-dimethoxy-2-pyrimidinyl)amino]carbonyl]amino]sulfonyl]-1-methyl-1H-pyrazole-4-carboxylate;

N-[[(4,6-dimethoxy-2-pyrimidinylamino)carbonyl]-3-(ethylsulfonyl)- 2-pyridinesulfonamide;

methyl 3-[[[[(4-methoxy-6-methyl-1,3,5-triazin-2-yl)amino]carbonyl]amino]sulfonyl]-2-thiophene-carboxylate (thifensulfuron methyl);

methyl 2-[[[[N-(4-methoxy-6-methyl-1,3,5-triazin-2-yl)-N-methylamino]carbonyl]amino]sulfonyl]benzoate (tribenuron methyl);

methyl 2-[[[[(4,6-dimethoxy-2-pyrimidinyl)amino]carbonyl]amino]sulfonyl]methyl]benzoate (bensulfuron methyl);

2-[[[[(4,6-dimethoxy-2-pyrimidinyl)amino]carbonyl]amino]sulfonyl]-N,N-dimethyl-3-pyridinecarboxamide (nicosulfuron); and methyl 2-[[[[[4,6-bis(difluoromethoxy)-2-pyrimidinyl]amino]carbonyl]amino]sulfonyl]benzoate.

Also preferred (Preferred 10) are compositions of Preferred 7 wherein the mixture comprises a sulfonylurea herbicide selected from the group in Preferred 9.

DETAILED DESCRIPTION OF THE INVENTION

One method of formulating a pesticide is to form a suspension of one or more active ingredients in an aqueous based medium and then use thickeners, such as macromolecules of the natural or synthetic type, and/or suspending agents, such as clays or oxides, to slow the rate at which the suspended particles settle. An overview of this approach is given in "Physical Stability of Suspension Concentrates", Th. F. Tadros, Advances in Colloid and Interface Science, 12 (1980). The present invention introduces a novel product form which incorporates at least one polyelectrolyte or ionic surfactant, in addition to or in place of suspending agents, to create an aqueous based, physically stable, reversible structured-fluid which will flow on application of shear and which will rebuild its structure on standing (i.e., are thixotropic).

The aqueous, reversible structured-fluid compositions of this invention are obtained by combination of a pesticidal component with the inert ingredients of the aqueous medium.

The pesticides which are deliverable in the reversible structured-fluids of this invention can be water-soluble or -insoluble, and can themselves be electrolytes or non-electrolytes of agricultural significance. Depending on additional criteria, such as the solubility of the pesticide or its chemical stability, agricultural, suitable organic or inorganic salts may also be incorporated without effecting the ability to achieve an aqueous, reversible structured-fluid pesticidal composition. Examples of suitable pesticides are listed below.

Herbicides such as acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N,N-di- 2-propenylacetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fluazifop-P, fluchloralin, flumetsulam, fluometuron, fluorochloridone, fluorodifen, fluoroglycofen, flupoxam, fluridone, fluroxypyr, fluzasulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metsulfuron methyl, methylarsonic acid, monoammonium salt of methylarsonic acid, (4-chloro-2-methylphenoxy)acetic acid, S,S'-dimethyl-2-(difluoromethyl)-4-(2-methylpropyl)-6-(trifluoromethyl)- 3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]- 2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-($\alpha,\alpha$-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, triallate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor, insecticides such as monocrotophos, carbofuran, tetrachlorvinphos, malathion, parathionmethyl, methomyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fonophos, isofenphos, methidathion, methamidophos, phosmet, phosphamidon, phosalone, pirimicarb, phorate, terbufos, trichlorfon, methoxychlor, bifenthrin, biphenate, cyfluthrin, fenpropathrin, fluvalinate, flucythrinate, tralomethrin, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, penconazole, propiconazole, uniconzole, flutriafol, prochloraz, pyrifenox, fenarimol, triadimenol, diclobutrazol, copper oxychloride, furalaxyl, folpet and flusilazol; nematocides such as aldoxycarb, fenamiphos and fosthietan; bactericides such as oxytetracyline, streptomycin and tribasic copper sulfate; and acaricides such as binapacryl, oxythioquinox, chlorobenzilate, dicofol, dienochlor, cyhexatin, hexythiazox, amitraz, propargite and fenbutatin oxide.

The "agriculturally suitable salts" include organic or inorganic salts which can be used to salt-out otherwise water-soluble ionic pesticides thereby rendering them insoluble. In the ease of sulfonylurea herbicides, wherein chemical stabilization can be achieved by the addition of salts, agriculturally suitable salts refer to carboxylic or inorganic acid salts, provided that the solubility in water of such carboxylic or inorganic acid salts is greater than or equal to 3% at 5° C. and a pH between 6 and 10, and further provided that a 0.1 molar solution of the carboxylic or inorganic acid salt has a pH between 6 and 10.

The component "polyelectrolyte" includes all water-swellable or water-soluble polymers which bear more than one ionic functional group per each macromolecule. The molecular weight of the polyelectrolytes of this invention can range from thousands to over a million and and can bear multiple positive or negative charges on the macromolecular backbone or attached pendant groups. "Surfactants" consist of molecules lower in molecular weight than polyelectrolytes which are surface active and which bear one or two charges per molecule.

Suitable polyelectrolytes of the invention can be either cationic or anionic. Non-limiting examples of cationic polyelectrolytes or charged surfactants include: polyacrylamides, such as aminomethylated polyacrylamide polymer having pendant dialkylated ammonium salt groups; primary, secondary or tertiary polyamines, such as ethoxylated octadecylamine-octadecylguanidine complexes; quaternary ammonium salts with or without ethoxylation, protons or alkyl groups; and primary, secondary or tertiary amine surfactants with or without ethoxylation, protons or alkyl groups.

Non-limiting examples of anionic polyelectrolytes include polymers having pendant acid functional groups and the ability to form salts such as: anionic polyacrylamides and acrylamide copolymers, such as the sodium salt of 2-propenamide and 2-propenoic acid; polycarbonates, such as polyacrylic acid, polymethacrylic and styrene maleic anhydride acid polymers and copolymers; polysulfonates, such as lignosulfonates and sulfonated polystyrene; and polyphosphates.

Product literature available from most vendors of polymeric materials and the following reference indicate which ones are polyelectrolytes and their tolerance for salt if present; Handbook of Water Soluble Gums and Resins, Robert L. Davidson, Ed. McGraw-Hill, 1980.

A "suspending agent" can be clay and oxide particulates which are traditionally used to retard settling in both aqueous and non-aqueous based suspensions. These solids are typically used to modify the viscosity of suspensions, but in combination with polyelectrolyte or ionic surfactant they can effectively be used to produce a reversible structured-fluid matrix to be used as a medium for the delivery of water-soluble or non-electrolyte pesticide active ingredients.

Both surfactants and polyelectrolytes can associate with themselves or other species in solution and also with the surfaces of particulates (e.g., pesticide, suspending agent) in suspension. In this invention, the ionic nature of the polyelectrolyte and surfactant is believed to be related to the ability to form a reversible structured-fluid in the presence of charged particles of active or inert suspending agents.

The term "aqueous medium" is defined as water plus the portion of water-soluble components which are in solution. The latter can, but does not necessarily, include, such components as agriculturally suitable salts, dispersants, wetting agents, antibacterials, crystal growth inhibitors, anti-freezing agents and low levels of thickeners provided that their presence does not interfere with the formation of the reversible structured-fluid. In order for the formation of the reversible structured-fluid, the sum of the pesticidal component and agriculturally suitable salt must not exceed 85% of the total weight percent of the formulation.

Reversible structured-fluids can be made in several ways depending on the nature of the pesticide active ingredient (electrolyte or non-electrolyte) and its water solubility. In almost all cases, some mechanical milling or intense mixing is required to form the suspension precursor to the reversible structured-fluid. In general, the insoluble active-ingredient is added to the medium as a micronized powder of less than 10 microns in size, on average, or as a coarser solid which is then reduced in size to below 10 microns, on average, by a wet milling process. In the former case, the ingredients can be mixed well by stirring to disperse the solids. If the micronized powder is present as aggregates wherein the primary particles are held together by forces strong enough to make stirring impractical, wet milling is required to break-up the aggregates and reduce the solids to the primary particle size.

Addition of the polyelectrolyte at any step in the preparation of the composition is acceptable, provided that the polyelectrolyte does not degrade during the wet milling step(s) and such a step is required. For example, U.S. Pat. No. 4,936,900 describes the need to wet mill sulfonylurea herbicides in the process of creating a suspension of chemically-stable particles in an aqueous high salt medium. If the stability to wet milling is not known, the effect of mechanical energy on the polyelectrolyte in question can be determined by comparing the properties of a formulation made by pre- and post-milling addition of the polymer.

The purpose of the dispersion process is to allow the medium to "wet" the surface of the particles and to displace the air between the particles. The efficiency of the wetting process can be greatly improved by adding wetting agent(s). A dispersant can also be added to serve the function of keeping the particles separated once they have been dispersed in the suspension to be reversibly structured. Dispersants serve a similar function once the reversible, structured-fluid is thinned and added to water or a spray tank mixture. The use and selection of dispersants and wetting agents are well-known in the art. See T. C. Patton, "Paint Flow and Pigment Dispersion," Wiley (1979). The function of these materials and the mechanical processes for forming dispersions and suspensions are also known in the art. See, for example, G. D. Parfitt, "Dispersion of Powders in Liquids," Applied Science Pub. Ltd. (1973); and Th. F. Tadros, "Advances in Colloid and Interface Science," 12 (1980).

1) In one embodiment of the invention, the pesticide is an electrolyte present in a high-salt aqueous medium as insoluble particles (e.g., a sulfonylurea active ingredient, or an agriculturally-suitable salt thereof). In these cases, an appropriate water-soluble or water-swellable polyelectrolyte or ionic surfactant, which is also compatible with the carboxylic or inorganic acid salts and which will not lead to chemical decomposition of the active ingredients, is added to the suspension such that a reversible structured-fluid results.

For insoluble pesticide particles which are weak acids, bases or salts (e.g., maneb and mancozeb fungicides) a water-soluble or water-swellable polyelectrolyte or ionic surfactant is added to the suspension to form a reversible structured-fluid. The interaction between the ionic-insoluble structured-fluid particulates and the polyelectrolyte or ionic surfactant is believed to be responsible for the reversible structured-fluid characteristics.

2) The present invention also comprises compositions in which non-electrolyte, active ingredients (e.g., hexazinone herbicide and methomyl insecticide) are soluble in the aqueous medium. In these cases a suspending agent, such as hydrophilic silica, is used in combination with a polyelectrolyte or ionic surfactant to form a reversible structured-fluid matrix. While the pesticide is not actually part of the network or matrix, the overall system in which the pesticide resides is the reversible structured-fluid.

3) Another embodiment of the invention are compositions comprising electrolyte pesticides which are soluble in water (e.g., the alkali metal or amine salts of 2,4-D or 2,4-DB, the mono(isopropylamine) salt of glyphosate, and the potassium salt of picloram) wherein the use of a suspending agent along with polyelectrolytes or ionic surfactants is necessary. Alternatively, the pesticide can in some cases be "salted-out" by the addition of organic or inorganic salts and rendered partially if not completely water-insoluble. For example, 2,4-D alkali metal or amine salts can be "salted-out" by the addition of inorganic salts rendering the pesticide insoluble. The insoluble salt can, in turn, be milled to form an aqueous suspension which is suitable for reversible structured-fluid formation by the addition of polyelectrolyte or ionic surfactant. In such cases, the addition of a suspending agent is not nessary.

4) For compositions of the present invention containing non-electrolyte, insoluble, particulate pesticides (e.g., cyanazine, carbendazim, captafol, carbaryl, etc.), suspending agents such as clays and oxides are required in combination with a polyelectrolyte or ionic surfactant to form a reversible structured-fluid. In these cases, the pesticide particulates are immobilized by the reversible structured-fluid matrix as it forms.

In essence, all the compositions of the instant invention incorporate at least one polyelectrolyte or ionic surfactant which is water-soluble or water-swellable and which retains its function as a fluid structuring agent if inorganic salts are present. In the case of sulfonylurea herbicides and their salts, where ammonium or alkali metal acid salts of a carboxylic or inorganic acid are required for chemical stability, the polyelectrolyte or ionic surfactant must retain its function as a fluid structuring agent in the presence of these salts and not destabilize the active sulfonylurea herbicide. In the case when salts are used to "salt-out" soluble pesticide electrolytes, the polyelectrolytes or ionic surfactant must retain its functionality as a fluid structuring agent, without resolubilization of the pesticide active. In the case when salt is required to enhance the functionality of the suspending agent, the polyelectrolytes or ionic surfactant must retain their functionality as a fluid structuring agent in the presence of these salts.

The effectiveness of the polyelectrolyte or ionic surfactant, and in some cases the suspending agent, is determined by comparison to a reference sample which does not contain one or more of these structuring agents.

Physical Measurements

The reversible structured-fluids are rigid at rest as reflected by their ability to retain a solid-like shape in an 8-ounce container at or near rest and show little or no sign of movement on tilting or on complete inversion of the container. The reversible structured-fluids of this invention are appreciably thinned by shaking, unlike gel or gelled-paste compositions which require vigorous shaking or mechanical agitation to assist their dispersion into water.

The thinning behavior of the reversible structured-fluid increases the ease with which the fluid disperses into water. The compositions of this invention are pourable once shaken, but will rebuild their structure on standing. On further dilution by water, the aqueous, reversible structured-fluid can be sprayed through conventional spray nozzles in which 50 mesh screens precede each nozzle to protect it from blockage.

By adjusting the amount of polyelectrolyte or ionic surfactant, the degree of reversibility and consistency of a reversible structured-fluid can be modified, spanning the range from that of an unstructured suspension to that of a gel or gelled-paste. However, the reversible structured-fluid is unique in its superior ability over than of a gel or gelled paste to disperse into water and its superior ability over that of a suspension to immobilize particulate matter.

In practice, verification of a reversible structured-fluid can be accomplished by experimental measurement and visual observation. The latter is the best method for differentiating reversible structured-fluids from suspension and gelled-paste controls. Visual observation requires a minimum of one observation of the composition on inversion through 180°, one observation of the composition on shaking, and one assessment of the ease of dispersion into water. In the case of unstructured suspensions, flow is observed on inversion, the suspensions pour easily, and the suspensions disperse homogeneously into water with stirring. At the other extreme, gels and gelled-pastes do not flow on inversion or after intense shaking, and do not disperse into water without intense mechanical agitation. The reversible structured-fluid pesticide compositions of this invention behave in a manner between these two extremes. They show no flow on 180° inversion, reduce to a liquid-like consistency with mild shaking, flow out of the container after shaking and disperse into water with little more than mild stirring, provided that thickeners have not been added at a level which retards the dispersion process. In such cases, more vigorous stirring may be required to achieve an agriculturally acceptable dispersion.

Viscosity and yield stress measurements are two additional measures used to quantify the extent of structure formation and pourability of a reversible structured-fluid. Both the viscosity and yield stress were measured using a rotational viscometer. Standard instruments are available from companies such as Haake, Contraves, Carri-Med, Bohlin and Brookfield. Both the instrument and accompanying geometry (parallel plate, cone and plate, concentric cylinder sample compartments) can be used to accurately measure yield stress and viscosity by one of the following techniques.

Either a fixed shear rate can be imposed on a sample and the resulting stress measured, or a controlled stress can be imposed on a sample and the resulting shear rate measured. A plot of the shear rate versus stress can be constructed and analyzed to extract the plastic viscosity and yield stress of the sample using the Bingham Equation. This is done by fitting the linear portion of the data to the equation. The slope of the plot gives the plastic viscosity of the sample and the intercept of the plot gives its yield stress. A more in-depth review of the an can be found in many texts on viscometry, rheology or rheometry. The following references contain such information: 1) K. Walters, "Rheometry: Industrial Applications," Research Studies Press (1980), 2) P. Sherman, "Industrial Rheology," Academic Press (1970), 3) T. C. Patton, "Paint Flow and Pigment Dispersion," Wiley (1979). Geometric constants, equations and instrumentation to automate instrument operation and calculation are supplied with the instruments mentioned above.

In general, the plastic viscosity and/or yield stress of a reversible structured fluid will be higher than those for an unstructured suspension and lower than those for a gel or gelled-paste. Thus, the measurement of yield stress and plastic viscosity can be used to evaluate the extent and degree of reversibility in structured-fluid compositions and to provide an additional tool with which to differentiate between unstructured suspensions, reversible structured-fluids, gels and gelled-pastes.

For assessing the effectiveness of the polyelectrolytes, ionic surfactants and suspending agent structuring systems, an aqueous unstructured control suspension wherein one or more of the structuring components were absent was used as a reference. On occasion, comparison was made to gelled-paste compositions to illustrate the difference between reversible, structured-fluids and a gelled-paste. In all cases, the following visual and rheological assessments were made:

Semi-rigidity, reflected by retention of shape in a container and resistance to flow when the container is inverted through 180°.

Fluidity, reflected by the ease with which a sample flows when subjected to shaking.

Phase separation, reflected by an ability to resist phase separation over time.

Restructuring, reflected by an ability to reform a semi-rigid structure within 24 hours after shaking.

One quantitative assessment of the effectiveness of the polyelectrolyte, ionic surfactant and, if present, suspending agent was the measurement plastic viscosity and yield stress. These rheological responses of the reversible structured-fluids were evaluated by the conventional rotational rheometry techniques previously described. A controlled stress rheometer equipped with a standard, calibrated, cup and bob geometry was used.

The measurement was taken by applying a range of stresses between 0.1 to 20 Pascals to a given sample in 20 logarithmic steps, from lowest to highest, with each stress allowed to act on the sample for 30 seconds before the next higher stress was applied. Using the shear stress—shear rate data collected, the Bingham Equation was applied and a yield stress and plastic viscosity were calculated by the methods described previously.

The selection of polyelectrolyte, ionic surfactant and, if needed, suspending agent was determined by comparing the reversible, structured fluid to a reference sample wherein the polymer was substituted by water. The polyelectrolyte, ionic surfactant and, if needed, suspending agent polymer(s) system is selected such that the beneficial effect is demonstrated:

a) by an increase in rigidity, consistency, fluidity, resistance to flow, and reduced phase separation as determined by visual inspection, or b) by an increase in viscosity as determined by viscosity measurement, or c) by an increase in yield stress as determined by yield stress measurement.

Comparisons to gels and gelled-paste compositions are also included for the purpose of illustrating the novel behavior of the reversible structured-fluid compositions.

EXAMPLES

The following examples are presented to illustrate, but in no way limit, the present invention. All percentages are given by weight.

The preparation of reversible structured-fluid compositions can be separated into two separate steps; formation of the dispersion followed by the addition of the structuring agent(s).

For sulfonylureas, a preferred technique for the preparation of stabilized dispersions has been described in U.S. Pat. No. 4,936,900. The procedure requires that the sulfonylurea be suspended in water and that a dispersant, thickener or suspending agent be added, followed by neutralization with a desired base such as ammonium or sodium hydroxide to a pH of 6.0–10.0, preferably 7.0–9.0, followed by addition of an insolubilizing salt, such as a carboxylic or inorganic acid salt(s), with agitation. This method of preparation is used in the instant invention with the following exception. Organic thickening agents are not required to demonstrate the reversible structured-fluid in its most basic form, since any additional antisettling agents would only complement the novel antisettling properties of the compositions of the instant invention.

All salts were added incrementally to the neutralized conjugate acids in order to develop the precipitated sulfonylurea salt slowly and to avoid the formation of a tacky solid or gum, per U.S. Pat. No. 4,936,900. The resulting suspension was then bead-milled to an average particle size of 1–20 microns, preferably 1–8 microns.

Polyelectrolyte and/or ionic surfactant structuring agent(s) were added after the milling step was completed to avoid the risk of degradation of the polymer during the high shear milling step.

Cases wherein a composition is not referred to as a control, the composition contains a polyelectrolyte and/or ionic surfactant structuring agent and is classified as a reversible structured-fluid. In all the examples which follow, the reversible structured-fluid can be visually described as being semi-rigid fluid which flows easily when subjected to shaking, and which restructures to a semi-rigid fluid within 24 hours after cessation of shaking. Conversely, the control unstructured dispersion to which the reversible structure-fluid is compared is always free flowing, showing no rigidity or resistance to flow. The reversible structured-fluids are also compared to gelled-paste systems which exhibit another extreme of flow behavior. These systems are also semi-rigid, like the reversible structured-fluid, however they do not spontaneously flow on shaking and their structure is ever-fast, showing instantaneous presence upon cessation of shaking.

The ingredients used in the following Examples, and their function, are as follows: Reax® 81A (sodium alkylnaphthalenesulfonate), an anionic wetting agent which can be used to insure proper wetting and milling of the active ingredient; 50% aqueous sodium hydroxide solution which can be used to adjust the pH of the slurry, as needed; and sodium acetate which can be used as the stabilizing organic salt for all aqueous sulfonylurea suspensions, per U.S. Pat. No. 4,936,900. A number of structuring agents can be used such as:

Armeen® OL=a primary alkylamine, cationic surfactant; Adogen® 425-50%=a 50% aqueous solution of a trimethyl soya quaternary ammonium chloride surfactant; Cat-Floc® L and Cat-Floc® TL=diallyl dimethyl quaternary ammonium chloride polyelectrolytes, and Nalcolyte® 603=a quaternary polyamine polyelectrolyte.

EXAMPLES 1–2

| Ingredients | Composition (wt. %) | | |
| --- | --- | --- | --- |
|  | Control | Ex. 1 | Ex. 2 |
| thifensulfuron methyl | 41.0 | 41.8 | 41.8 |
| sodium alkylnaphthalenesulfonate | 2.0 | 2.0 | 2.0 |
| aqueous 50% sodium hydroxide | 10.1 | 10.3 | 10.3 |
| sodium acetate (anhydrous) | 10.0 | 10.2 | 10.2 |
| water | 36.9 | 33.7 | 34.1 |
| Structuring Agent(s) - Nalcolyte ® 603 | — | 2.0 | 1.6 |

The sodium alkylnaphthalenesulfonate was dissolved in ~80–90% of the total water, at room temperature, with stirring. Thifensulfuron methyl was added incrementally, in three equal portions, and allowed to disperse well. The 50% aqueous sodium hydroxide solution was then added slowly over a 15 min. period with stirring to form the salt of the thifensulfuron methyl. Anhydrous sodium acetate was added in three steps, in a 1:1:2 ratio by weight. The additions were made at 30, 45 and 55 minutes during which time the slurry was continually stirred. The dispersion was then bead-milled for 30 min. Upon completion the structuring agent and/or water were added to achieve the above statement of composition. The final mixture was stirred until visually homogeneous.

The yield stress and plastic viscosity of each composition were measured as previously described. The results are tabulated below.

| System | Yield Stress (Pa) | Plastic Viscosity (Pa-s) |
| --- | --- | --- |
| Control (No Structuring Agent) | 1.0 | 0.05 |
| Ex. 1 Nalcolyte ® 603 | 35.1 | 0.55 |
| Ex. 2 Nalcolyte ® 603 | 38.2 | 0.20 |

The control sample was fluid at the time of preparation and did not form a semi-rigid structure over time. The control also formed 11% supernatant (bleed) over a 3 week period and remained freely moving, whereas the reversible structured-fluids (Ex. 1 and 2) showed no tendency to form bleed (less than 2–3%) and were semi-rigid (firm) within 24 h of preparation. The reversible structured-fluids would not move on tilting and required shaking to fluidize. The yield stress and plastic viscosity of the reversible structured-fluids were significantly greater than that of the control. From the data and visual characteristics of the reversible structure-fluids of these examples the ability to form a reversible structured-fluid of a sulfonylurea dispersion with a polyelectrolyte which retains its functionality in high salt medium is demonstrated.

To determine the effect of the polyelectrolyte on the chemical stability of the sulfonylurea, all samples were aged at 45° C. for 3 weeks. After aging, their chemical properties were assessed and compared. The results indicated that the structuring agent(s) did not impact the stability of the sulfonylurea when compared to the control. The stability of the latter is demonstrated in U.S. Pat. No. 4,936,900.

EXAMPLES 3–4

| Ingredients | Composition (wt. %) | | |
|---|---|---|---|
| | Control | Ex. 3 | Ex. 4 |
| thifensulfuron methyl | 41.0 | 41.4 | 41.8 |
| sodium alkylnaphthalenesulfonate | 2.0 | 2.0 | 2.0 |
| aqueous 50% sodium hydroxide | 10.1 | 10.2 | 10.4 |
| sodium acetate (anhydrous) | 10.0 | 10.1 | 10.2 |
| water | 36.9 | 35.3 | 33.8 |
| Structuring Agent(s) | | | |
| Armeen ® OL | — | 1.0 | — |
| Adogen ® 415-50% | — | — | 1.8 |

The compositions were prepared as described in Examples 1–2 and the final mixture was stirred until visually homogeneous. The yield stress and plastic viscosity of each composition were measured as previously described. The results are tabulated below.

| System | Yield Stress (Pa) | Plastic Viscosity (Pa-s) |
|---|---|---|
| Control (No Structuring Agent) | 1.0 | 0.05 |
| Ex. 3 Armeen ® OL | 28.9 | 0.44 |
| Ex. 4 Adogen ® 415-50% | 44.3 | 0.26 |

The control sample was fluid at the time of preparation and did not form a semi-rigid structure over time. The control also formed 11% supernatant (bleed) over a 3 week period and remained freely moving, whereas the reversible structured-fluids (Ex. 3 and 4) developed little more than a trace amount of bleed (less than 2–3%) and became semi-rigid (firm) within 24 h of preparation. The yield stress and plastic viscosity of the reversible structured-fluids were significantly greater than that of the control. The reversible structured-fluids would not move on tilting and required shaking to fluidize. From the data and visual characteristics of the reversible structure-fluids of these examples the ability to reversibly structure a sulfonylurea dispersion with a cationic surfactant which retains its functionality in high salt medium is demonstrated.

To determine the effect of the polyelectrolyte on the chemical stability of the sulfonylurea, all samples were aged at 45° C. for 3 weeks. After aging, their chemical properties were assessed and compared. The results indicated that the structuring agent(s) did not impact the stability of the sulfonylurea when compared to the control. The stability of the latter is demonstrated in U.S. Pat. No. 4,936,900.

EXAMPLES 5–6

| Ingredients | Composition (wt. %) | | |
|---|---|---|---|
| | Control | Ex. 5 | Ex. 6 |
| chlorsulfuron | 41.0 | 41.8 | 41.0 |
| sodium alkylnaphthalenesulfonate | 2.0 | 2.0 | 2.0 |
| aqueous 50% sodium hydroxide | 9.3 | 9.5 | 9.3 |
| sodium acetate (anhydrous) | 10.0 | 10.2 | 10.0 |
| acetic Acid | 0.5 | 0.5 | 0.5 |
| water | 37.2 | 33.0 | 34.5 |
| Structuring Agent(s) | | | |
| Cat Floc ® TL | — | 3.0 | — |
| Cat Floc ® L | — | — | 2.7 |

The sodium alkylnaphthalenesulfonate was dissolved in ~80–90% of the total water, at room temperature, with stirring. Chlorsulfuron was added incrementally, in three equal portions, and allowed to disperse well. The 50% aqueous sodium hydroxide solution was then added slowly over a 15 min. period with stirring to form the salt of the chlorsulfuron. Anhydrous sodium acetate was added in three steps, in a 1:1:2 ratio by weight. The additions were made at 30, 45 and 55 min. during which time the slurry was continually stirred. The dispersion was then bead-milled for 30 min. Upon completion the pH was adjusted to 8.3 with acetic acid, then structuring agent and/or water were added to achieve the above statement of composition. The final mixture was stirred until visually homogeneous. The yield stress and plastic viscosity of each composition were measured as previously described. The results are tabulated below.

| System | Yield Stress (Pa) | Plastic Viscosity (Pa-s) |
|---|---|---|
| Control (No Structuring Agent) | 1.0 | 0.02 |
| Ex. 5 Cat Floc ® TL | 30.3 | 0.08 |
| Ex. 6 Cat Floc ® L | 22.1 | 0.06 |

The control sample was fluid at the time of preparation and did not form a semi-rigid structure over time. The control also formed 15% supernatant (bleed) over a 3 week period and remained freely moving, whereas the reversible structured-fluids (Ex. 5 and 6) showed little or no tendency to form bleed (less than 2–3%) and were semi-rigid (firm) within 24 h of preparation. The reversible structured-fluids would not move on tilting and required shaking to fluidize. The yield stress and plastic viscosity of the reversible structured-fluids were significantly greater than that of the control. From the data and visual characteristics of the reversible structure-fluids of these examples the ability to form a reversible structured-fluid of a sulfonylurea dispersion with a polyelectrolyte which retains its functionality in high salt medium is demonstrated.

To determine the effect of the polyelectrolyte on the chemical stability of the sulfonylurea, all samples were aged at 45° C. for 3 weeks. After aging, their chemical properties were assessed and compared. The results indicated that the structuring agent(s) did not impact the stability of the sulfonylurea when compared to the control. The stability of the latter is demonstrated in U.S. Pat. No. 4,936,900.

EXAMPLES 7–9

|  | Composition (wt. %) | | |
|---|---|---|---|
| Ingredients | Ex. 7 | Ex. 8 | Ex. 9 |
| nicosulfuron | 41.0 | 21.0 | 0.0 |
| bromoxynil | 0.0 | 21.0 | 41.0 |
| sodium alkylnaphthalenesulfonate | 2.0 | 2.0 | 2.0 |
| aqueous 50% sodium hydroxide | 10.0 | 10.0 | 10.0 |
| sodium acetate (anhydrous) | 10.0 | 10.0 | 10.0 |
| water | 30.0 | 30.0 | 30.0 |
| Structuring Agent Adogen ® 415-50% | 7.0 | 6.0 | 6.0 |

The following process sequence represents a route to the formation of the reversible structured-fluids of Examples 7 to 9. The sodium alkylnaphthalenesulfonate is dissolved in 80–90% of the total water, at room temperature, with stirring. The technical active ingredients are added incrementally and disperse with mechanical agitation or stirring. The 50% aqueous sodium hydroxide solution is added slowly over a 15 min. period with stirring to form the active ingredient salts. Anhydrous sodium acetate is added stepwise to slowly salt-out a portion or all of the active ingredient. The additions are made over a 1 h period during which the slurry is continually stirred. The dispersion is then bead-milled for 30 min. Upon completion the structuring agent and/or water is added to achieve the above statement of composition. The final mixture is stirred until visually homogeneous.

The reversible structured-fluids of Examples 7–9 have yield stress and plastic viscosities in excess of compositions wherein the structuring agent is replaced by water, and have a maximum yield stress of 60 Pa and a maximum plastic viscosity of 5 Pa-s. The compositions are rigid at rest once the structure forms and do not flow on inversion through 180° when contained by an 8-ounce wide-mouth container which is at least ½ to ¾ full. They are easily fluidized by minimal shaking and completely disperse in water in 1–3 min., with mild stirring. The reversible structured-fluids of Examples 7–9 regain their rigidity within 24 h when returned to the rest state.

EXAMPLE 10

|  | Composition (wt. %) | |
|---|---|---|
| Ingredients | Control | Ex. 10 |
| Carbendazim | 19.8 | 19.8 |
| Alkanol ® XC | 1.0 | 1.0 |
| Aerosil ® 200 | 2.0 | 2.0 |
| Water | 77.2 | 76.4 |
| Structuring Agent Nalcolyte ® 603 | 0.0 | 0.8 |

The following sequence represents a route to the formation of the reversible structured-fluid of Example 10. The Carbendazim was added to the water as an air-milled powder of approximately 2 microns in mean average particle size followed by the addition of Alkanol® XC. The mixture was then stirred for 5 minutes using an overhead paddle stirrer. During this time, a uniform suspension was attained. The Aerosil® 200 was then added and stirring continued for an additional 5 minutes. At this point and for several hours thereafter the composition was extremely fluid like. The sample was then split into two equal portions. The balance of water to 100% was added to one portion with stirring to create a control. Nalcolyte® 603 was added to the second portion with continued stirring to create the reversible structured-fluid. The final mixtures were visually homogeneous.

The yield stress and plastic viscosity of the control and reversible structured-fluid were measured as previously described. The results are tabulated below.

| System | Yield Stress (Pa) | Plastic Viscosity (Pa-s) |
|---|---|---|
| Control | 0.28 | 0.005 |
| Ex. 10 Nalcolyte ® 603 | 7.73 | 0.041 |

The control sample was fluid at the time of preparation and did not form a semi-rigid structure over time. The control also formed ~50% supernatant (bleed) over a 24 hour period and remained freely flowing, whereas the reversible structured-fluid of Example 10 showed only a trace of bleed (<2–3%) and was semi-rigid exhibiting no tendency to flow on tilting, but being rapidly thinned by shaking. The yield stress and plastic viscosity of the reversible structured-fluid were significantly greater than those of the control. From the data and visual characteristics of the reversible structured-fluid of Example 10, the ability to form a reversible structured-fluid of a fungicide dispersion where the active ingredient is a non-electrolyte, insoluble material was demonstrated.

EXAMPLES 11 and 12

|  | Composition (wt. %) | | |
|---|---|---|---|
| Ingredients | Control | Ex. 11 | Ex. 12 |
| Mancozeb Technical | 29.4 | 29.4 | 29.4 |
| Aerosil ® 200 | 2.0 | 2.0 | 2.0 |
| Water | 68.6 | 66.6 | 65.6 |
| Structuring Agent Nalcolyte ® 603 | 0.0 | 2.0 | 3.0 |

The following sequence represents a route to the formation of the reversible structured-fluids of Examples 11 and 12. Technical mancozeb powder of particle size less than 20 microns was added to the water and stirred for 20 minutes with an overhead paddle stirrer. During this time, the powder wetted and a uniform suspension was attained. The Aerosil® 200 was then added and stirring was continued for an additional 55 minutes. The composition at this point was extremely fluid like. The sample was then split into three equal portions. Water was added to one portion with stirring to create a control. Nalcolyte® 603 was added to the second and third portions with continued stirring to create the reversible structured-fluids. The final mixtures were visually homogeneous.

The yield stress and plastic viscosity of the control and reversible structured-fluid were measured as previously described. The results are tabulated below.

| System | Yield Stress (Pa) | Plastic Viscosity (Pa-s) |
| --- | --- | --- |
| Control | 0.91 | 0.099 |
| Ex. 11 Nalcolyte ® 603 at 2% | 1.27 | 0.039 |
| Ex. 12 Nalcolyte ® 603 at 3% | 1.50 | 0.003 |

The control sample was fluid at the time of preparation and did not form a semi-rigid structure over time. The control also formed ~8% supernatant (bleed) over a 24 hour period and remained freely flowing, whereas the reversible structured-fluid of Examples 11 and 12 showed only a trace of bleed (<2–3%) and were semi-rigid exhibiting no tendency to flow on tilting, but being rapidly thinned by shaking. The yield stress and plastic viscosity of the reversible structured-fluids were significantly greater than those of the control. The data and visual characteristics of the reversible structured-fluids of Examples 11 and 12 demonstrate the ability to form a reversible structured-fluid of a fungicide dispersion where the active ingredient is an insoluble electrolyte.

EXAMPLE 13

| | Composition (wt. %) | |
| --- | --- | --- |
| Ingredients | Control | Ex. 13 |
| Glyphosate | 19.8 | 19.8 |
| Aerosil ® 200 | 4.0 | 4.0 |
| Water | 75.2 | 74.2 |
| Structuring Agent Nalcolyte ® 603 | 0.0 | 1.0 |

The following sequence represents a route to the formation of the reversible structured-fluid of Example 13. Technical glyphosate air-milled powder, approximately 2 micron in mean average particle size, was added to the water and stirred for ~60 minutes using an overhead paddle stirrer. During this time the powder dissolved into the water forming a clear solution. The Aerosil® 200 was then added and stirring was continued for an additional 30 minutes. The composition at that time was fluid-like and lacked color. The sample was then split into two equal portions. Water was added to one portion with stirring to create the control. Nalcolyte® 603 was added to the second portion with continued stirring to create the reversible structured-fluid. The final mixtures were visually homogeneous.

The yield stress and plastic viscosity of the control and reversible structured-fluid were measured as previously described. The results are tabulated below.

| System | Yield Stress (Pa) | Plastic Viscosity (Pa-s) |
| --- | --- | --- |
| Control | 0.63 | 0.85 |
| Ex. 13 Nalcolyte ® 603 | 2.18 | 0.54 |

The control sample was fluid at the time of preparation and did not form a semi-rigid structure over time. The control remained freely flowing, whereas the reversible structured-fluid of Example 13 was semi-rigid exhibiting no tendency to flow on tilting, but being rapidly thinned by shaking. The yield stress and plastic viscosity of the reversible structured-fluid were significantly greater than those of the control. Example 13 demonstrates the ability to form a reversible structured-fluid of a herbicide where the active ingredient is a soluble non-electrolyte.

EXAMPLE 14

| | Composition (wt. %) | |
| --- | --- | --- |
| Ingredients | Control | Ex. 14 |
| Chlorsulfuron | 21.0 | 21.0 |
| Sodium alkylnaphthalenesulfonate | 1.0 | 1.0 |
| Aqueous 50% sodium hydroxide | 4.5 | 4.5 |
| Sodium acetate (anhydrous) | 10.0 | 10.0 |
| Aerosil ® 200 | 2.0 | 2.0 |
| Water | 61.5 | 59.5 |
| Structuring Agent Adogen ® 415-50% | 0.0 | 2.0 |

The sodium alkylnaphthalenesulfonate was dissolved in ~80–90% of the total water, at room temperature, with stirring. The Chlorsulfuron herbicide was added incrementally, in three equal portions, with stirring, and allowed to disperse well. The 50% aqueous sodium hydroxide solution was then added slowly over a 30 min. period with stirring to form the salt of the Clorosulfuron, raising the pH of the mixture to ~8.0. Anhydrous sodium acetate was then added in three portions, in a 1:1:2 ratio by weight. The additions were made at 30, 60, and 80 min. from the time of the final 50% aqueous sodium hydroxide addition. Stirring was continued for another 15 minutes after which the pH was adjusted to 8.0 by using a minute amount of an aqueous 50% sodium hydroxide solution. With continued stirring, the Aerosil® 200 was added and mixed for 15 minutes. The resulting slurry was visually homogeneous. The dispersion was then bead-milled for 30 minutes. Upon completion, Adogen® 415 and/or water were added to achieve the above statements of composition. The final mixture was stirred until visually homogeneous. The yield stress and plastic viscosity of each composition were not measured. The samples were however exposed to a series of aging tests to assess their stability via and alternative and reasonably standard test in the industry.

The control sample was fluid at the time of preparation and formed 12%, 21%, and 16% supernatant (bleed) on storage for three weeks at 45° C., room temperature and –6° C., respectively. Conversely, the reversible structured-fluid of Example 14 showed almost no signs of bleed when stored under the same conditions. The reversible structured-fluid of Example 14 was fluid at the time of preparation, but formed a semi-rigid structure within 24 hours which exhibited no tendency to flow on tilting and which rapidly thinned on shaking. The yield stress and plastic viscosity of the reversible structured fluid were significantly greater than those of the control. The data and visual characteristics of the reversible structured-fluid of Example 14 demonstrate the ability to form a reversible structured-fluid of a sulfonylurea herbicide at relatively low rates of active ingredient with a high resistance to the formation of bleed over long periods of time and at extremes in temperature.

EXAMPLES 15–17

| Ingredients | Composition (Wt. %) | | | |
| --- | --- | --- | --- | --- |
|  | Control | Ex. 15 | Ex. 16 | Ex. 17 |
| nicosulfuron | 7.2 | 7.2 | 7.2 | 7.2 |
| bromoxynil | 34.5 | 34.5 | 34.5 | 34.5 |
| sodium alkylnaphthalenesulfonate | 2.0 | 2.0 | 2.0 | 2.0 |
| aqueous 50% sodium hydroxide | 3.8 | 3.8 | 3.8 | 3.8 |
| sodium acetate (anhydrous) | 10.0 | 10.0 | 10.0 | 10.0 |
| water | 42.5 | 41.0 | 40.5 | 42.1 |
| structuring agent |  |  |  |  |
| Nalcolyte ® 603 | 0.0 | 1.5 | 2.0 | 0.0 |
| Adogen ® 415-50% | 0.0 | 0.0 | 0.0 | 0.4 |

The sodium alkylnaphthalenesulfonate was dissolved in ~80–90% of the total water, with stirring. The nicosulfuron herbicide was added incrementally, in three equal portions, with stirring, and allowed to disperse well. The 50% aqueous sodium hydroxide solution was then added slowly over a 20 minute period with stirring to form the salt of the nicosulfuron, raising the pH of the mixture to ~9.1. Anhydrous sodium acetate was then added in three steps, in a 1:1:2 ratio, by weight. The additions were made at 30, 53, and 73 minutes from the time the final 50% aqueous sodium hydroxide was added. Stirring was continued for another 15 minutes after which the pH was measured at 8.9. With continued stirring, the bromoxynil was added and mixed for 20 minutes. At this time more 50% aqueous sodium hydroxide solution was added to bring the pH to between 8.5–9.0. The resulting slurry was visually homogeneous. The dispersion was then bead-milled for 30 minutes. Upon completion Nalcolyte® 603 and/or Adogen® 415 and/or water were added to achieve the above statements of composition. The final mixture was stirred until visually homogeneous. The yield stress and plastic viscosity of the control and reversible structured-fluid were measured as previously described. The results are tabulated below.

| System | Yield Stress (Pa) | Plastic Viscosity (Pa-s) |
| --- | --- | --- |
| Control | 3.02 | 0.035 |
| Ex. 15 Nalcolyte ® 603 at 1.5% | 4.91 | 0.089 |
| Ex. 16 Nalcolyte ® 603 at 2.0% | 9.04 | 0.121 |
| Ex. 17 Adogen ® 415-50% at 0.42% | 5.56 | 1.082 |

The control sample was fluid at the time of preparation and formed some structure over time, but not a semi-rigid structure per Examples 15–17. When the control sample was tilted 90° the sample structure resisted for an instant then turned fluid compared to the reversible structured-fluid of Examples 15–17 that were semi-rigid exhibiting no tendency to flow on tilting 180°, but being rapidly thinned (fluidizing) by shaking. The control also formed ~3% supernatant (bleed) over a 15 hour period, whereas the reversible structured-fluid of Examples 15–17 only showed minute bleed (<0.25%). The yield stress and plastic viscosity of the reversible structured-fluids were significantly greater than that of the control. The data and visual characteristics of the reversible structured-fluids of Examples 15–17 demonstrate the ability to form a reversible structured-fluid using a mixture of widely diverse crop protection chemicals.

What is claimed is:

1. A thixotropic pesticidal formulation comprising a pesticidal component, a structuring agent, and the balance to 100% being an aqueous medium wherein:

the pesticidal component is selected from the group:
   a) a soluble electrolyte,
   b) a soluble non-electrolyte,
   c) an insoluble electrolyte, and
   d) an insoluble non-electrolyte; and and the structuring agent is at least one anionic or cationic member selected from the group:
   e) a polyelectrolyte,
   f) a surfactant, and
   g) a suspending agent; provided that:

(i) when the pesticidal component is a), b) or d), then the structuring agent is g) and at least one of e) and f), such that e) and g) bear dissimilar charges, or when e) is not present, f) and g) bear dissimilar charges;

(ii) when the pesticidal component is c), then the structuring agent is selected from at least one of e) and f), such that e) and c) bear dissimilar charges, or when e) is not present, f) and c) bear dissimilar charges;

the ingredients being present in the following amounts based on total weight of the formulation:

1–60% pesticidal component;

0.1–20% of at least one of a polyelectrolyte and a surfactant;

0–20% suspending agent; the combination of pesticide, polyelectrolyte, surfactant, and suspending agent at least 4%; and 35–96% aqueous medium.

2. A formulation according to claim 1 wherein the pesticidal component is a herbicide and the ingredients are present in the following amounts based on total weight of the formulation:

10–50% herbicide;

0.1–10% at least one of a polyelectrolyte and a surfactant;

0–15% suspending agent; and

35–96% aqueous medium.

3. A formulation according to claim 2 wherein the pesticidal component is a sulfonylurea herbicide and the ingredients are present in the following amounts based on total weight of the formulation:

10–40% sulfonylurea;

0.1–5% of at least one of a polyelectrolyte and a surfactant;

0–10% suspending agent;

5–25% agriculturally suitable stabilizing salt, and

35–96% aqueous medium.

4. A formulation according to claim 3 wherein the sulfonylurea is a sulfonylurea of Formula I

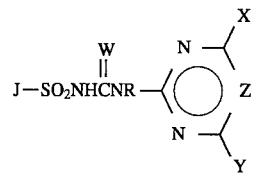

wherein:

J is

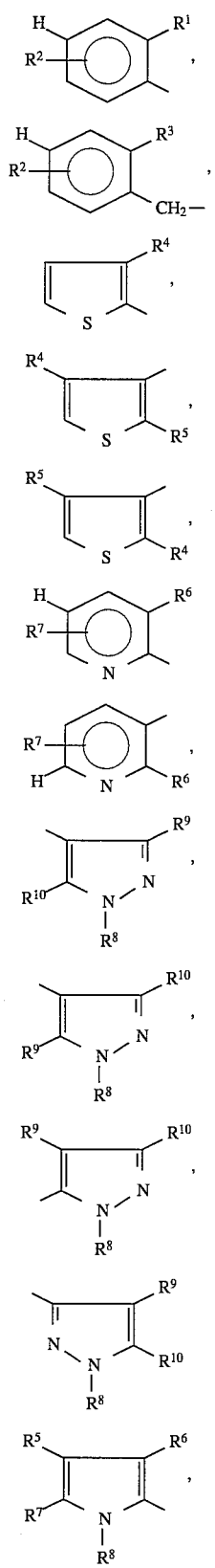

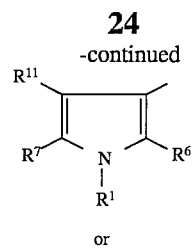

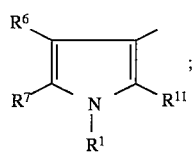

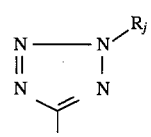

R is H or CH$_3$;

R$^1$ is F, Cl, Br, NO$_2$, C$_1$–C$_4$ alkyl, C$_1$–C$_4$ haloalkyl, C$_3$–C$_4$ cycloalkyl, C$_2$–C$_4$ haloalkenyl, C$_1$–C$_4$ alkoxy, C$_1$–C$_4$ haloalkoxy, C$_2$–C$_4$ alkoxyalkoxy, CO$_2$R$^{12}$, C(O)NR$^{13}$R$^{14}$, SO$_2$NR$^{15}$R$^{16}$, S(O)$_n$R$^{17}$, C(O)R$^{18}$, CH$_2$CN or L;

R$^2$ is H, F, Cl, Br, CN, CH$_3$, OCH$_3$, SCH$_3$, CF$_3$ or OCF$_2$H;

R$^3$ is Cl, NO$_2$, CO$_2$CH$_3$, CO$_2$CH$_2$CH$_3$, SO$_2$N(CH$_3$)$_2$, SO$_2$CH$_3$, SO$_2$CH$_2$CH$_3$, OCH$_3$, or OCH$_2$CH$_3$;

R$^4$ is C$_1$–C$_3$ alkyl, C$_1$–C$_2$ haloalkyl, C$_1$–C$_2$ alkoxy, C$_2$–C$_4$ haloalkenyl, F, Cl, Br, NO$_2$, CO$_2$R$^{12}$, C(O)NR$^{13}$R$^{14}$, SO$_2$NR$^{15}$R$^{16}$, S(O)$_n$R$^{17}$, C(O)R$^{18}$ or L;

R$^5$ is H, F, Cl, Br or CH$_3$;

R$^6$ is C$_1$–C$_3$ alkyl, C$_1$–C$_2$ alkoxy, C$_2$–C$_4$ haloalkenyl, F, Cl, Br, CO$_2$R$^{12}$, C(O)NR$^{13}$R$^{14}$, SO$_2$NR$^{15}$R$^{16}$, S(O)$_n$R$^{17}$, C(O)R$^{18}$ or L;

R$^7$ is H, F, Cl, CH$_3$ or CF$_3$;

R$^8$ is H, C$_1$–C$_3$ alkyl or pyridyl;

R$^9$ is C$_1$–C$_3$ alkyl, C$_1$–C$_2$ alkoxy, F, Cl, Br, NO$_2$, CO$_2$R$^{12}$, SO$_2$NR$^{15}$R$^{16}$, S(O)$_n$R$^{17}$, OCF$_2$H, C(O)R$^{18}$, C$_2$–C$_4$ haloalkenyl or L;

R$^{10}$ is H, Cl, F, Br, C$_1$–C$_3$ alkyl or C$_1$–C$_2$ alkoxy;

R$^{11}$ is H, C$_1$–C$_3$ alkyl, C$_1$–C$_2$ alkoxy, C$_2$–C$_4$ haloalkenyl, F, Cl, Br, CO$_2$R$_{12}$, C(O)NR$^{13}$R$^{14}$, SO$_2$NR$^{15}$R$^{16}$, S(O)$_n$R$^{17}$, C(O)R$^{18}$ or L;

R$^{12}$ is C$_1$–C$_3$ alkyl optionally substituted by halogen, C$_1$–C$_2$ alkoxy or CN, allyl or propargyl;

R$^{13}$ is H, C$_1$–C$_3$ alkyl or C$_1$–C$_2$ alkoxy;

R$^{14}$ is C$_1$–C$_2$ alkyl;

R$^{15}$ is H, C$_1$–C$_3$ alkyl, C$_1$–C$_2$ alkoxy, allyl or cyclopropyl;

R$^{16}$ is H or C$_1$–C$_3$ alkyl;

R$^{17}$ is C$_1$–C$_3$ alkyl, C$_1$–C$_3$ haloalkyl, allyl or propargyl;

R$^{18}$ is C$_1$–C$_4$ alkyl, C$_1$–C$_4$ haloalkyl or C$_3$–C$_5$ cycloalkyl optionally substituted by halogen;

n is 0, 1 or 2;

L is

R$_j$ is H or C$_1$–C$_3$ alkyl;

W is O or S;

X is H, $C_1$–$C_4$ alkyl, $C_1$–$C_4$ alkoxy, $C_1$–$C_4$ haloalkoxy, $C_1$–$C_4$ haloalkyl, $C_1$–$C_4$ haloalkylthio, $C_1$–$C_4$ alkylthio, halogen, $C_2$–$C_5$ alkoxyalkyl, $C_2$–$C_5$ alkoxyalkoxy, amino, $C_1$–$C_3$ alkylamino or di($C_1$–$C_3$ alkyl)amino;

Y is H, $C_1$–$C_4$ alkyl, $C_1$–$C_4$ alkoxy, $C_1$–$C_4$ haloalkoxy, $C_1$–$C_4$ alkylthio, $C_1$–$C_4$ haloalkylthio, $C_2$–$C_5$ alkoxyalkyl, $C_2$–$C_5$ alkoxyalkoxy, amino, $C_1$–$C_3$ alkylamino, di($C_1$–$C_3$ alkyl)amino, $C_3$–$C_4$ alkenyloxy, $C_3$–$C_4$ alkynyloxy, $C_2$–$C_5$ alkylthioalkyl, $C_2$–$C_5$ alkylsulfinylalkyl, $C_2$–$C_5$ alkylsulfonylalkyl, $C_1$–$C_4$ haloalkyl, $C_2$–$C_4$ alkynyl, $C_3$–$C_5$ cycloalkyl, azido or cyano;

Z is CH or N;

and their agriculturally suitable salts; provided that:

(a) when X and/or Y is $C_1$ haloalkoxy, then Z is CH;

(b) when X is halogen, then Z is CH and Y is $OCH_3$, $OCH_2CH_3$, $N(OCH_3)CH_3$, $NHCH_3$, $N(CH_3)_2$ or $OCF_2H$.

5. A formulation according to claim 4 wherein the sulfonylurea is selected from the group:

2-chloro-N-[[(4-methoxy-6-methyl-1,3,5-triazin-2-yl)amino]carbonyl]benzenesulfonamide (chlorsulfuron);

methyl 2-[[[[(4,6-dimethyl-2-pyrimidinyl)amino]carbonyl]amino]sulfonyl]benzoate (sulfometuron methyl);

ethyl 2-[[[[(4-chloro-6-methoxy-2-pyrimidinyl)amino]carbonyl]amino]sulfonyl]benzoate (chlorimuron ethyl);

methyl 2-[[[[(4-methoxy-6-methyl-1,3,5-triazin-2-yl)amino]carbonyl]amino]sulfonyl]benzoate (metsulfuron methyl);

methyl 2-[[[[(4,6-dimethoxy-2-pyrimidinyl)amino]carbonyl]amino]sulfonyl]-6-(trifluoromethyl)-3-pyridinecarboxylate (ethametsulfuron methyl);

methyl 2-[[[[4-ethoxy-6-(methylamino)-1,3,5-triazin-2-yl]amino]carbonyl]amino]sulfonyl]benzoate;

2-(2-chloroethoxy)-N-[[(4-methoxy-6-methyl-1,3,5-triazin-2-yl)amino]carbonyl]benzenesulfonamide;

ethyl 5-[[[[(4,6-dimethoxy-2-pyrimidinyl)amino]carbonyl]amino]sulfonyl]-1-methyl-1H-pyrazole-4-carboxylate;

N-[[(4,6-dimethoxy-2-pyrimidinylamino]carbonyl]-3-(ethylsulfonyl)- 2 -pyridinesulfonamide;

methyl 3-[[[[(4-methoxy-6-methyl-1,3,5-triazin-2-yl)amino]carbonyl]amino]sulfonyl]-2-thiophene-carboxylate (thifensulfuron methyl);

methyl 2-[[[[N-(4-methoxy-6-methyl-1,3,5-triazin-2-yl)-N-methylamino]carbonyl]amino]sulfonyl]benzoate (tribenuron methyl);

methyl 2-[[[[[(4,6-dimethoxy-2-pyrimidinyl)amino]carbonyl]amino]sulfonyl]methyl]benzoate (bensulfuron methyl);

2-[[[[(4,6-dimethoxy-2-pyrimidinyl)amino]carbonyl]amino]sulfonyl]-N,N-dimethyl-3-pyridinecarboxamide (nicosulfuron); and methyl 2-[[[[4,6-bis(difluoromethoxy)-2-pyrimidinyl]amino]carbonyl]amino]sulfonyl]benzoate.

6. A formulation of claim 1 wherein the pesticide is an insecticide.

7. A formulation of claim 1 wherein the pesticide is a fungicide.

8. A method for protecting crops comprising applying to the crop to be protected an effective mount of a formulation according to claim 1.

9. A formulation of claim 2 wherein the pesticidal component comprises a sulfonylurea herbicide and a non-sulfonylurea pesticide in the following mounts based on total weight of the formula:

10–40% sulfonylurea and non-sulfonylurea pesticide;

0.1–5% at least one of a polyelectrolyte and a surfactant;

0–10% suspending agent;

5–25% agriculturally suitable stabilizing salt, such that the sulfonylurea and stabilizing salt are less than 85% by total formulation weight; and 35–96% aqueous medium.

10. A formulation of claim 9 wherein the pesticidal component comprises a sulfonylurea herbicide and 3,5-dibromo-4-hydroxybenzonitrile.

* * * * *

UNITED STATES PATENT AND TRADEMARK OFFICE
CERTIFICATE OF CORRECTION

PATENT NO. : 5,538,936
DATED : July 23, 1996
INVENTOR(S) : Clarence G. Hermansky It is certified that error appears in the above-indentified patent and that said Letters Patent is hereby corrected as shown below:

At Col. 2, line 63 change "85%" to --65--%.

At Col. 3, line 10 change "85%" to --65--%.

At Col. 7, line 13 change "agricultural," to --agriculturally--.

At Col. 8, line 34 change "ease" to --case--.

At Col. 9, line 35 change "85%" to --65--%.

At Col. 10, line 30 change "structured-fluid" to --pesticide--.

Signed and Sealed this

Twentieth Day of May, 1997

Attest:

BRUCE LEHMAN

Attesting Officer    Commissioner of Patents and Trademarks